United States Patent

Byker et al.

Patent Number: 6,141,137
Date of Patent: Oct. 31, 2000

[54] ELECTROCHROMIC MEDIA FOR PRODUCING A PRESELECTED COLOR

[75] Inventors: Harlan J. Byker; Thomas F. Guarr, both of Holland; Derick D. Winkle, Zeeland, all of Mich.

[73] Assignee: Gentex Corporation, Zeeland, Mich.

[21] Appl. No.: 09/299,490

[22] Filed: Apr. 26, 1999

Related U.S. Application Data

[63] Continuation-in-part of application No. 09/140,310, Aug. 26, 1998, Pat. No. 6,037,471.

[51] Int. Cl.⁷ .............................................. G02F 1/15
[52] U.S. Cl. ........................... 359/265; 359/272; 359/273; 252/583
[58] Field of Search .................................... 359/265, 272, 359/273, 275, 321, 322; 252/583, 600

[56] References Cited

U.S. PATENT DOCUMENTS

| | | | |
|---|---|---|---|
| 4,902,108 | 2/1990 | Byker . | |
| 5,128,787 | 7/1992 | Blonder | 359/70 |
| 5,204,778 | 4/1993 | Bechtel | 359/604 |
| 5,278,693 | 1/1994 | Theiste et al. | 359/272 |
| 5,280,380 | 1/1994 | Byker | 359/265 |
| 5,282,077 | 1/1994 | Byker | 359/272 |
| 5,294,376 | 3/1994 | Byker | 252/600 |
| 5,336,448 | 8/1994 | Byker | 252/583 |
| 5,434,407 | 7/1995 | Bauer et al. | 250/227.24 |
| 5,448,397 | 9/1995 | Tonar | 359/272 |
| 5,451,822 | 9/1995 | Bechtel et al. | 359/267 |
| 5,679,283 | 10/1997 | Tonar et al. | 252/583 |
| 5,881,431 | 3/1999 | Pieper, II et al. | 16/82 |
| 5,888,431 | 3/1999 | Tonar et al. | 252/583 |
| 5,928,572 | 7/1999 | Tonar et al. | 252/583 |
| 6,020,987 | 2/2000 | Baumann et al. | 359/273 |
| 6,037,471 | 3/2000 | Srinivasa et al. | 546/257 |

FOREIGN PATENT DOCUMENTS

WO 98 42 796   10/1998   WIPO .

OTHER PUBLICATIONS

Application for International No. PCT/WO97/EP498 titled Electrochromic System.
Application for International No. PCT/WO98/EP3862 titled Elektrochrome Polymersysteme.
English translations of the abstract and examples 2–14 of PCT/WO98/EP3862.

*Primary Examiner*—Loha Ben
*Attorney, Agent, or Firm*—Brian J. Rees

[57] ABSTRACT

Electrochromic compositions suitable for use in electrochromic media in electrochromic devices contain minimally two electrochromic compounds of the same redox type, whose redox potentials are greater than 30 mV. The lower redox potential electrochromic compound makes a large contribution to the absorbancy of the electrochromic medium despite being present in only minor concentration.

32 Claims, 1 Drawing Sheet

ELECTROCHROMIC MEDIA FOR PRODUCING A PRESELECTED COLOR

CROSS-REFERENCE TO RELATED APPLICATIONS

This application is a continuation-in-part of U.S. patent application Ser. No. 09/140,310, filed Aug. 26, 1998, now U.S. Pat. No. 6,037,471.

TECHNICAL FIELD

The present invention is directed to electrochromic devices. More particularly, the present invention pertains to improved electrochromic media capable of producing a preselected color.

BACKGROUND ART

Electrochromic devices, and electrochromic media suitable for use therein, are the subject of numerous U.S. patents, including U.S. Pat. No. 4,902,108, entitled "Single-Compartment, Self-Erasing, Solution-Phase Electrochromic Devices, Solutions for Use Therein, and Uses Thereof", issued Feb. 20, 1990 to H. J. Byker; Canadian Pat. No. 1,300,945, entitled "Automatic Rearview Mirror System for Automotive Vehicles", issued May 19, 1992 to J. H. Bechtel et al.; U.S. Pat. No. 5,128,799, entitled "Variable Reflectance Motor Vehicle Mirror", issued Jul. 7, 1992 to H. J. Byker; U.S. Pat. No. 5,202,787, entitled "Electro-Optic Device:, issued Apr. 13, 1993 to H. J. Byker et al.; U.S. Pat. No. 5,204,778, entitled "Control System For Automatic Rearview Mirrors", issued Apr. 20, 1993 to J. H. Bechtel; U.S. Pat. No. 5,278,693, entitled "Tinted Solution-Phase Electrochromic Mirrors", issued Jan. 11, 1994 to D. A. Theiste et al.; U.S. Pat. No. 5,280,380, entitled "UV-Stabilized Compositions and Methods", issued Jan. 18, 1994 to H. J. Byker; U.S. Pat. No. 5,282,077, entitled "Variable Reflectance Mirror", issued Jan. 25, 1994 to H. J. Byker; U.S. Pat. No. 5,294,376, entitled "Bipyridinium Salt Solutions", issued Mar. 15, 1994 to H. J. Byker; U.S. Pat. No. 5,336,448, entitled "Electrochromic Devices with Bipyridinium Salt Solutions", issued Aug. 9, 1994 to H. J. Byker; U.S. Pat. No. 5,434,407, entitled "Automatic Rearview Mirror Incorporating Light Pipe", issued Jan. 18, 1995 to F. T. Bauer et al.; U.S. Pat. No. 5,448,397, entitled "Outside Automatic Rearview Mirror for Automotive Vehicles", issued Sep. 5, 1995 to W. L. Tonar; and U.S. Pat. No. 5,451,822, entitled "Electronic Control System", issued Sep. 19, 1995 to J. H. Bechtel et al., each of which patents is assigned to the assignee of the present invention and the disclosures of each of which are hereby incorporated herein by reference, are typical of modern day automatic rearview mirrors for motor vehicles. These patent references describe electrochromic devices, their manufacture, and electrochromic compounds useful therein, in great detail.

While numerous electrochromic devices are possible, the greatest interest and commercial importance are associated with electrochromic windows, light filters and mirrors. A brief discussion of these devices will help to facilitate an understanding of the present invention.

Electrochromic devices are, in general, prepared from two parallel substrates coated on their inner surfaces with conductive coatings, at least one of which is transparent such as tin oxide, or the like. Additional transparent conductive materials include fluorine doped tin oxide (FTO), tin doped indium oxide (ITO), ITO/metal/ITO (IMI) as disclosed in "Transparent Conductive Multilayer-Systems for FPD Applications", by J. Stollenwerk, B. Ocker, K. H. Kretschmer of LEYBOLD AG, Alzenau, Germany, and the materials described in above-referenced U.S. Pat. No. 5,202,787, such as TEC 20 or TEC 15, available from Libbey Owens-Ford Co. (LOF) of Toledo, Ohio. Co-filed U.S. patent application entitled "AN IMPROVED ELECTRO-OPTIC DEVICE INCLUDING A LOW SHEET RESISTANCE, HIGH TRANSMISSION TRANSPARENT ELECTRODE" describes a low sheet resistance, high transmission, scratch resistant transparent electrode that forms strong bonds with adhesives, is not oxygen sensitive, and can be bent to form convex or aspheric electro-optic mirror elements or tempered in air without adverse side effects. The disclosure of this commonly assigned application is hereby incorporated herein by reference.

The two substrates of the device are separated by a gap or "cavity", into which is introduced the electrochromic medium. This medium contains at least one anodic or cathodic electrochromic compound which changes color upon electrochemical oxidation or reduction, and at least one additional electroactive species which may be reduced or oxidized to maintain charge neutrality. Upon application of a suitable voltage between the electrodes, the electroactive compounds are oxidized or reduced depending upon their redox type, changing the color of the electrochromic medium. In most applications, the electroactive compounds are electrochromic compounds which change from a colorless or near colorless state to a colored state. Upon removal of the potential difference between the electrodes, the electrochemically activated redox states of electroactive compounds react, becoming colorless again, and "clearing" the window.

Many improvements to electrochromic devices have been made. For example, use of a gel as a component of the electrochromic medium, as disclosed in U.S. Pat. Nos. 5,679,283 and 5,888,431, both entitled "Electrochromic Layer and Devices Comprising Same", and U.S. application Ser. No. 08/616,967, entitled "Improved Electrochromic Layer And Devices Comprising Same", now U.S. Pat. No. 5,928,572, have allowed the preparation of larger devices which are also less subject to hydrostatic pressure.

In electrochromic mirrors, devices are constructed with a reflecting surface located on the outer surface of the substrate which is most remote from the incident light (i.e. the back surface of the mirror), or on the inner surface of the substrate most remote from the incident light. Thus, light striking the mirror passes through the front substrate and its inner transparent conductive layer, through the electrochromic medium contained in the cavity defined by the two substrates, and is reflected back from a reflective surface as described previously. Application of voltage across the inner conductive coatings results in a change of the light reflectance of the mirror.

In electrochromic devices, the selection of the components of the electrochromic medium is critical. The medium must be capable of reversible color changes over a life cycle of many years, including cases where the device is subject to high temperatures as well as exposure to ultraviolet light. Thus, the industry constantly seeks new electrochromic media and new electroactive compounds which will resist aging, particularly in exterior locations. The effects of ultraviolet light, in particular, are felt more strongly when the electroactive compounds contained in electrochromic media are energized to their respective oxidized and reduced states.

In addition to problems associated with device stability over time, devices of improved color have been desired. The colors heretofore obtainable were limited both by the stability of available electrochromic compounds as well as economic factors such as their commercial availability and expense. Moreover, in many applications, for example electrochromic mirrors, it is desirable that the mirror, both in its inactive as well as its active state, be a relatively neutral color, for example gray. In addition, it is desirable that the color can be maintained over a range of voltage, for example, that the absorbance of the electrochromic medium may be changed without undesirably changing the hue, in particular between "full dark" and "clear" conditions.

Prior art electrochromic media generally employed two electrochromic compounds, one anodic and one cathodic, and were unable to acceptably produce gray shades, and numerous other shades of color as well. In U.S. application Ser. No. 08/832,596 filed Apr. 2, 1997, now U.S. Pat. No. 6,020,987 herein incorporated by reference, non-staging devices capable of achieving a preselected color are disclosed. These devices contain at least three active materials, at least two of which are electrochromic compounds, and exhibit little or no staging while being available in neutral colors such as gray, or in other preselected colors not normally available.

In accordance with the '596 disclosure, when two or more anodic electrochromic compounds are used, the redox potentials of the anodic electrochromic compounds should be relatively closely matched to prevent staging. The same is true if the electrochromic medium contains two or more cathodic electrochromic compounds; the redox potential of these should be relatively closely matched as well. This required close matching of redox potentials limits the choices available for electrochromic compounds. Thus, many electrochromic compounds which are relatively less expensive or which exhibit greater stability cannot be used when certain target colors and/or devices are envisioned because their redox potentials are unsuitable and prevent their being used in an electrochromic device.

It would be desirable to prepare electrochromic devices which are highly stable, which allow for a wide choice of electroactive compounds, and which are capable of being manufactured in a wide range of preselected colors, all at commercially acceptable cost.

DISCLOSURE OF INVENTION

It has now been surprisingly discovered that electrochromic devices capable of producing a pre-selected color may be prepared employing at least three electroactive compounds, two of which are of the same redox type and another which is of a complementary redox type, where one of said two electroactive compounds of the same redox type has a more easily accessible electrochemically activated redox state. The latter contributes to the absorption spectrum of the electrochemically activated state of the medium to a greater extent than would be expected based solely on its abundance in the medium.

BEST MODE FOR CARRYING OUT THE INVENTION

Figure 1A:
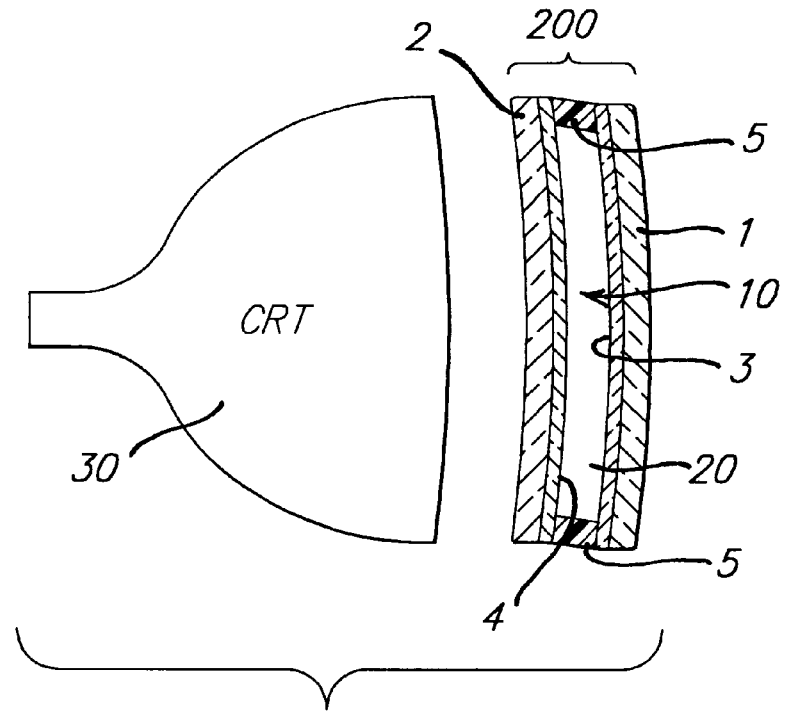
FIG. 1A illustrates an electrochromic filter suitable for application in front of a CRT or other display.

The electrochromic media of the present invention comprise at least three electroactive materials having absorption spectra, when electrochemically activated, which add together such that the color of the electrochromic medium can be pre-selected by individually choosing the concentrations of the at least three electroactive materials. The at least three electroactive materials include at least one reducible material (cathodic material), at least one oxidizable material (anodic material) and at least one additional electroactive material which may be either an anodic or cathodic material. Thus, there are always three electroactive materials present in the medium, with at least two either being anodic or cathodic materials. Generally, all three electroactive materials are electrochromic such that there is a change in the absorption coefficient at at least one wavelength in the visible spectrum when electrochemically activated. However, there are instances where it is desirable to have at least two electrochromic materials combined with at least one generally colorless electroactive material. In any case, at least two of the electroactive materials in the medium must be electrochromic.

The present invention may be understood with reference to a conventional electrochromic medium containing two electrochromic compounds. In such a medium, an anodic electrochromic compound, i.e. an electrochromic compound which is electrochemically oxidizable at the anode, is combined with a cathodic electrochromic compound, i.e. an electrochromic compound which is reducible at the cathode. Upon application of a suitable voltage, the anodic materials, examples of which are the various substituted 5,10-dihydrophenazines, are oxidized, to an oxidized state which has a higher extinction coefficient at at least one wavelength in the visible region of the spectrum as compared to the unoxidized compound. At the same time, a cathodic electrochromic compound, for example a bipyridinium salt (a "viologen"), is reduced, preferably by a one electron reduction, to a visible light-absorbing reduced state.

The absorption spectra of the electrochromic compounds, when electrochemically activated, must add together such that the color of the electrochromic medium can be pre-selected by individually choosing the concentrations of the electroactive materials. In a stable device, every electron that is removed through oxidation of an anodic material must be balanced by one electron that is accepted through reduction of a cathodic material. Thus in an electrochromic medium containing three or more electroactive materials, the total number of electrons transferred at the anode must equal the total number of electrons transferred at the cathode. This limitation is an important aspect in ensuring the ability to produce a pre-selected color in accordance with the present invention.

To illustrate this point, it is well known that one may add blue to yellow to make green, however, if an anodic material with a change from colorless to dark blue on oxidation, and a cathodic material with a change from colorless to light yellow on reduction, are added together they will always produce an electrochromic medium with the same hue throughout its normal voltage range regardless of the ratios of the concentrations of the anodic and cathodic materials. This is because the total amount of anodic material oxidized must be equal to the total amount of cathodic material reduced. Thus, even if the amount of the cathodic material that turns yellow on reduction is doubled or even tripled, the color will remain the same, because for every cathodic species that turns yellow, one anodic species will turn blue. However, in order for the concentration of both the cathodic electroactive materials and the anodic electroactive materials to be current limiting in solution-phase systems, the total concentration of one type may be different from the total concentration of the other type due to differences in diffusion coefficients in the electrochromic medium. Often the material(s) with smaller diffusion coefficients are present at slightly higher concentrations.

In U.S. application Ser. No. 08/832,596, previously cited, an improvement in electrochromic devices has been the introduction of an electrochromic medium comprising at least three electroactive compounds (at least two of which are electrochromic). Thus, the envisioned mixtures would have concentrations of electrochemically activated species approximately in proportion to their abundance in the medium.

It has now been surprisingly discovered, however, that when electroactive compounds of the same redox type are purposefully selected such that their redox potentials differ by greater than 30 mV, preferably greater than 40 mV, the more easily oxidizable/reducible electroactive compound will contribute to the absorption spectrum of the device from its clear state to its full dark state, to an extent greater than expected based solely on its abundance in the medium. This surprising result allows for additional combinations of electroactive compounds not previously thought possible. Moreover, because only a very minor amount of the more easily oxidizable/reducible electroactive compound is necessary to achieve the preselected color, electroactive compounds which would otherwise not be suitable for commercial use may be exploited.

It should be noted that the "differences" in redox potential discussed herein are actually the absolute value of the differences in redox potential of electroactive compounds of the same type, i.e., two or more anodic electroactive compounds, or two or more cathodic electroactive compounds. Only two electroactive compounds of the same redox type whose absolute value of redox potential difference exceeds 30 mV need be present. Additional electroactive compounds of the same redox type, but whose redox potential is less than 30 mV different from either or both of the foregoing two electroactive compounds may be present as well.

Without wishing to be bound to any particular theory, applicants believe that an equilibrium between species of the same redox type exists. For example, for two anodic electroactive compounds, one having a high redox potential ($A_H$) and another having a low redox potential ($A_L$), the equilibrium between their redox states may be represented by

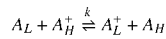

$$A_L + A_H^+ \overset{k}{\rightleftharpoons} A_L^+ + A_H$$

where $A^+$ represents the charged, single electron oxidized species. The equilibrium lies to the right, in favor of the charged low redox potential species $A_L^+$.

The net effect is that a much higher relative proportion of electroactive compounds with low redox potential are elevated to the oxidized state. For example, in a medium with only one anodic electrochromic compound, only 30% of the electrochromic compound molecules may be oxidized at any given time. In a medium with two anodic electroactive compounds of differing redox potential, of the total of the oxidized anodic species $[A_H^+]$ and $[A_L^+]$, perhaps 80% will be $[A_L^+]$ species derived from the electrochromic compound of lower redox potential. Thus, electroactive components with a more easily accessible electrochemically activated state will make a more significant contribution to the absorbance spectrum of the medium than one would attribute based solely on their abundance in the medium.

This enhanced contribution to the spectrum of the medium is a direct result of the fact that its electrochemically activated state is more easily accessible and is present in higher relative proportions than the mole ratio of the unactivated form to the total material of its redox type in the medium. This mole ratio is less than 28 mol percent, preferably below 25 mol percent, and most preferably below 20 mol percent.

While the above discussion has centered on anodic electroactive compounds, the same applies to cathodic electroactive compounds as well. Species derived from the more easily reduced electroactive compound will dominate the absorbance spectrum to a greater extent than can be attributed relative to its concentration. The more easily redoxible electroactive compounds can be selected for their color contribution and stability rather than cost, since they are used in minor amount.

The difference in redox potential between electroactive compounds of the same redox type should preferably be greater than 30 mV. However, it is also preferable that the actual upper limit be such that the applied voltage to the cell is lower than the second electron redox potential for electroactive compounds where the difference between first and second redox potentials is appreciable. Although some disproportionation of electroactive compounds and other electroactive species may ordinarily result in some concentration of more highly oxidized and reduced states, it is generally desired to minimize the concentration of these species.

The amount of lower redox potential electrochromic compounds of a given redox type may vary, but is preferably less than 50 mol percent of total electroactive compound of the same redox type, more preferably less than 35 mol percent, and is preferably in the range of 0.1 mol percent to 40 mol percent, more preferably 1 mol percent to 30 mol percent, and most preferably in the range of 5 mol percent to 30 mol percent. Mol percentage concentrations of ca. 7–28 mol percent have been shown to be quite effective with anodic electrochromic compounds of lower redox potential, while mol percentage concentrations of ca. 11 mol percent have been shown to be quite effective with cathodic electrochromic compounds of lower redox potential. Lower, in the sense used herein with respect to redox potential, is in terms of the absolute value of the redox potential.

Anodic and cathodic electrochromic compounds of numerous types are known, and their redox potentials published or easily measured. Particularly preferred electrochromic compounds are anodic electrochromic compounds of the dihydrophenazine type, and cathodic electrochromic compounds of the bipyridinium type. Wavelengths of maximum absorbtion and extinction coefficients of many electrochromic compounds can be found in U.S. application Ser. No. 09/140,310, incorporated herein by reference.

As stated above, the electrochromic medium of the present invention preferably comprise at least three electroactive materials having absorption spectra in their activated state which add together such that a pre-selected color of the electrochromic medium can be made by individually choosing the concentrations of the at least three electroactive materials contained in the medium. This pre-selected color may be a wide range of perceived colors, such as red, orange, yellow, green, blue, gray, etc.

In the following Tables, a number of cathodic electrochromic materials and a number of anodic electrochromic materials are listed which, when dissolved in a suitable solvent or solvent medium which includes enough dissolved electrolyte to provide ionic conductivity to the solution, can be used as solution-phase electrochromic materials. The solvents used are generally polar, aprotic organic solvents taught in U.S. Pat. No. 4,902,108. In a number of these solvents, the materials in the Tables exhibit two chemically reversible waves in a cyclic voltammogram run at an inert electrode at room temperature. The first cyclic voltammogram wave generally is due to a one electron per molecule reduction or one electron per molecule oxidation which is accompanied by a change from colorless or slightly colored to significantly colored (i.e. light absorbing at least one wavelength in the visible spectrum). The use of these materials in electrochromic devices is normally restricted to the one electron oxidized state. These reduced states for cathodic materials or oxidized states for anodic materials have a particular light absorption spectrum that generally follow Beer's law throughout their range of concentrations in activated electrochromic devices, with the exception of some materials which at higher concentrations of the reduced state show complication in the spectrum due to what is believed to be dimerization.

As long as the voltage applied to an electrochromic device containing these materials is restricted to the normal range in which only the first electrochemically activated state is produced at the electrodes, the materials will make a consistent color contribution varying only in the amount of absorption. If the voltage is too large, the color or visible light absorption spectrum of the twice reduced state(s) and/or twice oxidized state(s) will contribute to the overall spectrum of the electrochromic medium and therefore the electrochromic device. Going outside the normal voltage range may and often will result in a perceived change in color of the medium. For several of the materials in the Tables, the difference in redox potential for the first one electron reduction and the second one electron reduction is quite small and therefore the normal voltage range for a device containing these materials is quite limited.

The redox potentials give an indication of the ease of accessibility of the electrochemically activated state, thus the first compound in the table with a listed redox potential of –0.100V has a more easily accessible electrochemically activated state than the last entry of the table with a listed potential of –0.492V.

TABLE 1

|  | $E_{1/2}$ |
|---|---|
| 1,1'-diphenyl-4,4'-dipyridinium bis(tetrafluoroborate) | –0.100 |
| 1,1'-bis(2,6-dimethylphenyl)-4,4'-dipyridinium bis(tetrafluoroborate) | –0.112 |
| 1.1'-bis(3,5-dimethylphenyl)-4,4'-dipyridinium bis(tetrafluoroborate) | –0.116 |
| 1-phenyl-1'-(4-dodecylphenyl)-4,4'-dipyridinium bis(hexafluorophosphate) | –0.116 |
| 1,1'-bis(2,4,6-trimethylphenyl)-4,4'-dipyridinium bis(tetrafluoroborate) | –0.116 |
| 1-(4-cyanophenyl)-1'-methyl-4,4'-dipyridinium bis(hexafluorophosphate) | –0.132 |
| 1-(3,5-dimethoxyphenyl)-1'-methyl-4,4'-dipyridinium bis(hexafluorophosphate) | –0.192 |
| 1-methyl-1'-phenyl-4,4'-dipyridinium bis(hexafluorophosphate) | –0.204 |
| 1-methyl-1'-(2-methylphenyl)-4,4'-dipyridinium bis(hexafluorophosphate) | –0.216 |
| 1-(4-methoxyphenyl)-1'-methyl-4,4'dipyridinium bis(hexafluorophosphate | –0.216 |
| 1-methyl-1'-(2,4,6-trimethylphenyl)-4,4'-dipyridinium bis(hexafluorophosphate) | –0.216 |
| 1,2,6-trimethyl-1'-phenyl-4,4'-dipyridinium bis(tetrafluoroborate) | –0.276 |
| 1,1'-dimethyl-2,6-diphenyl-4,4'-dipyridinium bis(tetrafluoroborate | –0.292 |
| 1,1'-bis(3-phenyl(n-propyl))-4,4'-dipyridinium bis(tetrafluoroborate) | –0.296 |

TABLE 1-continued

|  | $E_{1/2}$ |
|---|---|
| 1,1'-dimethyl-4,4'-dipyridinium bis(tetrafluoroborate) | –0.304 |
| 1,1'-dimethyl-2-(3-phenyl(n-propyl))-4,4'-dipyridinium bis(hexafluorophosphate) | –0.340 |
| 1,1'-dimethyl-4,4'-(1,3,5-triazine-2,4-diyl)dipyridinium diperchlorate | –0.352 |
| 1,1'-dibenzyl-2,2',6,6'-tetramethyl-4,4'-dipyridinium bis(tetrafluoroborate) | –0.360 |
| 1,1'-dimethyl-2,2'-bis(3-phenyl(n-propyl))-4,4'-dipyridinium bis(tetrafluoroborate) | –0.376 |
| 1,1'-dimethyl-2,2'-bis(3-phenyl(n-propyl))4,4'-dipyridinium bis(tetrafluoroborate | –0.376 |
| 1,6-diethyl-1,6-diazapyrene-2,5,7,10-tetraketone | –0.424 |
| 1,1',2,2',3,3',4,4'-octahydro-8,8'-biquinolizinium bis(tetrafluoroborate) | –0.436 |
| 1,1',2-trimethyl-2',6,6'-tris(2-phenylethyl)-4,4'-dipyridinium bis(tetrafluoroborate) | –0.436 |
| 2,6-dimethylbenzoquinone | –0.472 |
| 1,4-dihydroxyanthraquinone | –0.472 |
| 1-methyl-4-(1,3,5-triazine-2-yl-10-pyridinium hexafluorophosphate | –0.472 |
| 1,1',2,2',6-pentamethyl-6'-n-hexyl-4,4'-dipyridinium bis(hexafluorophosphate | –0.484 |
| 1,1',2,2'-tetramethyl-6,6'-bis-n-hexyl-4,4'-dipyridinium bis(hexafluorophosphate) | –0.488 |
| 1,1',2,2',6-pentamethyl-6'-(3-phenyl(n-propyl))-dipyridinium bis(hexafluorophosphate) | –0.492 |

Table 2 lists anodic electrochromic materials and redox potentials for the first electrochemical oxidation for each material, these materials, in a similar manner to Table 1 are listed by accessibility of the electrochemically activated state, and the first entry with a listed redox potential of 0.256V has a more easily accessible electrochemically activated state than the last entry with a listed potential of 0.352V.

TABLE 2

|  | $E_{1/2}$ |
|---|---|
| N,N,N',N'-tetramethyl-p-phenylenediamine | 0.256 |
| 2,5,10-trimethyl-3-phenyl-5,10-dihydrophenazine | 0.260 |
| 5-ethyl-10-methyl-5,10-dihydrophenazine | 0.264 |
| 5,10-dimethyl-5,10-dihydrobenzo(A)phenazine | 0.264 |
| 2,7-diphenoxy-5,10-dimethyl-5,10-dihydrophenazine | 0.290 |
| 2-phenoxy-5,10-dimethyl-5,10-dihydrophenazine | 0.292 |
| 2,7-bis(o-tolyl)-5,10-dimethyl-5,10-dihydrophenazine | 0.292 |
| 2,3-dimethyl-7-trifluoromethyl-5,10-diethyl-5,10-dihydrophenazine | 0.292 |
| 5,10-dimethyl-5,10-dihydrophenazine | 0.300 |
| 2,3-diphenyl-5,10-dimethyl-5,10-dihydrophenazine | 0.300 |
| 2,7-diphenyl-5,10-dimethyl-5,10-dihydrophenazine | 0.300 |
| 2-vinyl-5,10-dimethyl-5,10-dihydrophenazine | 0.300 |
| 2-phenyl-5,10-dimethyl-5,10-dihydrophenazine | 0.308 |
| 5,10-diisopropyl-5,10-dihydrophenazine | 0.344 |
| 5,10-dimethyl-5,10-dihydrodibenzo(A,C)phenazine | 0.344 |
| 1,5,10-trimethyl-2-phenyl-5,10-dihydrophenazine | 0.348 |
| 2,3,5,10-tetramethyl-7-trifluoromethyl-5,10-dihydrophenazine | 0.348 |
| 2,3,5,10-tetramethyl-5,10-dihydrobenzo(B)phenazine | 0.352 |

Further examples of dihydrophenazine electrochromic compounds and method of their preparation may be found in copending U.S. application Ser. No. 09/280,396, herein incorporated by reference.

"Electrochromic compound", when used in the singular, denotes a single compound, or a compound and its isomers, and minor impurities which are not routinely separated. For example, in the reaction of 4-methyl catechol with 3-methyl-1,2-phenylene diamine followed by N-methylation of the resulting mixture of 5,10-dihydrophenazines, the product mixture will unavoidably contain both 3,5,6,10-tetramethyl- 5,10-dihydrophenazine and 1,5,8,10-tetramethyl-5,10-dihydrophenazine isomers, which are generally not separated. This mixture is considered a single electrochromic compound for the purposes of the present application.

By "anodic electroactive compound" is denoted an electroactive compound which is electrochemically oxidized at the anode of an electrochemical device. By "cathodic electrochromic compound" is meant a electrochromic compound which is electrochemically reduced at the cathode of an electrochromic device.

By the term "same redox type" is meant that two or more electroactive compounds are all anodic electroactive compounds, or all cathodic electrochromic compounds. In other words, all anodic electroactive compounds in an electrochemical device will be of the same "redox type".

The electrochromic medium includes electroactive anodic and cathodic materials and may be contained in solution in the ionically conducting electrolyte and remain in solution in the electrolyte when electrochemically oxidized or reduced. The electroactive materials may be contained in the continuous solution phase of a free standing gel in accordance with the teachings of U.S. patent application Ser. No. 08/616,967, entitled "Improved Electrochromic Layer And Devices Comprising Same" and International Patent Application Serial No. PCT/US98/05570 entitled "Electrochromic Polymeric Solid Films, Manufacturing Electrochromic Devices Using Such Solid Films, And Processes For Making Such Solid Films And Devices". The anodic and cathodic materials can be combined or linked by a bridging unit as described in International Application Serial No. PCT/WO97/EP498 entitled "Electrochromic System".

Additionally, the anodic and cathodic materials can be incorporated into the polymer matrix as described in International Application Serial No. PCT/WO981EP3862 entitled "Electrochromic Polymer System" and International Patent Application Serial No. PCT/US98/05570 entitled "Electrochromic Polymeric Solid Films, Manufacturing Electrochromic Devices Using Such Solid Films, And Processes For Making Such Solid Films And Devices".

In addition, the electrochromic medium may also contain other materials such as solvents, light absorbers, light stabilizers, thermal stabilizers, antioxidants, thickeners or viscosity modifiers or supporting electrolytes.

By the term "electrochromic device" is meant a device having at least one transparent substrate and a further substrate which between them define a cavity of substantially constant thickness such that the transmission/absorbance is substantially the same over different portions of the device when similarly energized. For planar mirrors, for example, the two glass panes which define the cavity should be substantially parallel. For curved or aspheric windows or mirrors, unless special effects are desired, the cavity should have a relatively constant depth in a direction orthogonal to the respective substrate inner, cavity-defining surfaces.

Electrochromic devices of the present invention are useful as rear-view mirrors for automobiles, windows, indicia display devices, light filters, and filters for displays, such as LCD, CRT, LED, etc. The use as a display filer is particularly effective, since a gray filter is highly desirable to provide displays with improved contrast ratios under a variety of lighting conditions as described by de Vries in "Electrochromics And Cathode Ray Tubes" (IME-3 abstracts, September 1998). For example, it is envisioned that a gray electrochromic device can be incorporated into the design of a CRT either by lamination of an assembled device to the viewing side of a CRT or through use of the CRT as one substrate of the electrochromic device.

FIG. 1A shows a cross-sectional view of an electrochromic light filter associated with a CRT display. The electrochromic filter 200 includes two transparent elements 1 and 2 each with a transparent conductive coating 3,4 on the inward surface, and a seal or gasket 5 around the perimeter of the device which defines a cavity 10 into which the electrochromic medium 20 is confined. The device then can be laminated or otherwise attached to the viewing surface of a CRT display 30 to reduce the amount of glare due to ambient light.

Figure 1B:
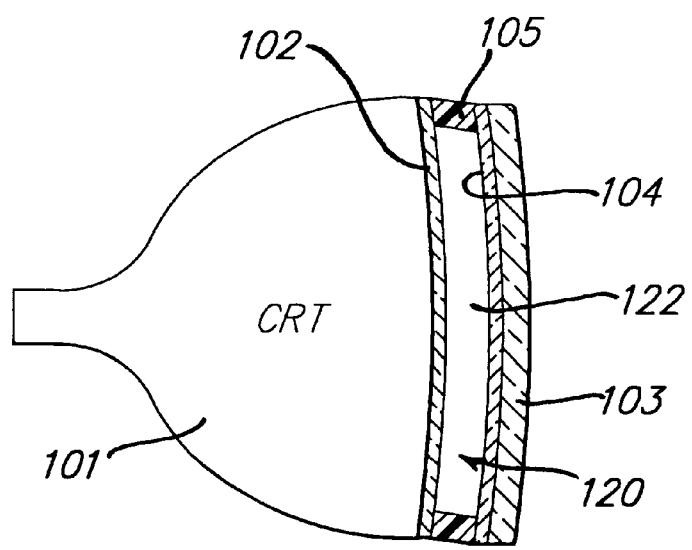
FIG. 1B illustrates a CRT having an integral electrochromic filter.

FIG. 1B shows a cross-sectional view of an electrochromic light filter made integral with a CRT display. The CRT 101 can be coated with a transparent conductive coating 102. A transparent cover 103 with a transparent conductive coating 104 is attached. A seal or gasket 105 defines a cavity 120 which contains the electrochromic medium 122.

The readability of a display such as a CRT or LCD device can be compromised by high ambient lights levels due to diffuse reflectance of the incident ambient light by the highly scattering inner surface of the display screen. The use of dark glass in the display screen (transmission level typically 30 to 70%) improves the contrast between emitted and reflected light, at the cost of higher power consumption and decreased resolution. A variable transmittance light filter, on the other hand, allows the CRT to be operated with low power in low ambient lighting conditions and with high power in high ambient lighting conditions, thereby decreasing power usage and increasing resolution of the CRT. A variable transmittance light filter further enhances the contrast between emitted and reflected light by decreasing the transmission level below 30%, and if necessary, to 20% or even 10%.

Having generally described this invention, a further understanding can be obtained by reference to certain specific examples which are provided herein for purposes of illustration only and are not intended to be limiting unless otherwise specified. In the examples and comparative examples which follow, electrochromic window devices are fabricated as is known in the art with TEC-15 glass from Libby-Owens-Ford with a 137 micrometer cell spacing. These devices measure about 1.5"×3" and are filled with the electrochromic solutions described in the examples and comparative examples via a two-hole fill technique. The fill holes are plugged with hot-melt glue. Note that direct comparative examples are identified by a "C" and followed by the example numeral to which they correspond.

EXAMPLE 1 AND COMPARATIVE EXAMPLE C1

Electrochromic media with the electrochromic compound compositions shown below are prepared in propylene carbonate and deoxygenated with dry nitrogen.

| | |
|---|---|
| Comparative Example C1) | 28mM 5,10-dimethyl-5,10-dihydrophenazine, 34mM 1,1'-bisphenyl-4,4'-dipyridinium bis(tetra-fluoroborate). |
| Example 1) | 20mM 5,10-dimethyl-5,10-dihydrophenazine, 8mM 2,3-diphenyl-5,10-diethyl-5,10-dihydrophenazine (28.6 mol percent), 34mM 1,1'-bisphenyl-4,4'-dipyridinium bis(tetra-fluoroborate). |

Application of 1.2V across each of the electrochromic devices results in uniform coloration. The device containing electrochromic medium C1 changes from light yellow to bright green, while the device containing electrochromic medium 1 changes from light tan to dull grayish-green. There is no staging noticed during darkening or clearing.

EXAMPLE 2 AND COMPARATIVE EXAMPLE C2

Electrochromic media with the electrochromic compound compositions shown below are prepared in propylene carbonate and deoxygenated with dry nitrogen.

| | |
|---|---|
| Comparative Example C2) | 28mM 2-vinyl-5,10-dimethyl-5,10-dihydrophenazine, 34mM 1,1'-ethylene-4,4'-dimethyl-2-dipyridinium bis(hexafluorophosphate) |
| Example 2) | 20mM 2-vinyl-5,10-dimethyl-5,10-dihydrophenazine, 8mM 2,3-diphenyl-5,10-diethyl-5,10-dihydrophenazine (28.6 mol percent), 34mM 1,1'-ethylene-4,4'-dimethyl-2,2' dipyridinium bis(hexafluorophosphate). |

Application of 1.2V across each of the electrochromic devices results in uniform coloration. The device containing electrochromic medium C2 changes from light yellow to dull yellow-tan, while the device containing electrochromic medium 2 changes from light yellow to rust-orange. There is no staging noticed during darkening or clearing.

EXAMPLE 3

An electrochromic medium containing a electrochromic compound composition consisting of 22 mM 5,10-dimethyl-5,10-dihydrophenazine, 6 mM 2-methyl-3-phenyl-5,10-dimethyl-5,10-dihydrophenazine (21 mol percent), and 34 mM 1,1'-bis(phenylpropyl)-4,4'-dipyridinium bis (tetrafluoroborate) in propylene carbonate is deoxygenated with dry nitrogen.

Application of 1.2V across the electrochromic device containing the electrochromic medium of Example 3 results in uniform coloration. The device changes from colorless to blue-gray. There is no staging noticed during darkening or clearing.

EXAMPLE 4

An electrochromic medium containing a electrochromic compound composition consisting of 21.5 mM 5,10-dimethyl-5,10-dihydrophenazine, 6.5 mM 2,5,7,10-tetramethyl-5,10-dihydrophenazine (23 mol percent), and 34 mM 1,1'-bis(phenylpropyl)-4,4'-dipyridinium bis (tetrafluoroborate) in propylene carbonate is deoxygenated with dry nitrogen.

Application of 1.2V across the electrochromic device containing the electrochromic medium of Example 4 results in uniform coloration. The device changes from colorless to blue-gray. There is no staging noticed during darkening or clearing.

EXAMPLE 5

An electrochromic medium containing a electrochromic compound composition consisting of 20 mM 5,10-dimethyl-5,10-dihydrophenazine, 8 mM 2-tertbutyl-5,7,10-trimethyl-5,10-dihydrophenazine (28.6 mol percent), and 34 mM 1,1'-bis(phenylpropyl)-4,4'-dipyridinium bis (tetrafluoroborate) in propylene carbonate is deoxygenated with dry nitrogen.

Application of 1.2V across the electrochromic device containing the electrochromic medium of Example 5 results in uniform coloration. The device changes from colorless to blue-gray. There is no staging noticed during darkening or clearing.

EXAMPLE 6

An electrochromic medium containing a electrochromic compound composition consisting of 26 mM 5,10-dimethyl-5,10-dihydrophenazine, 2 mM 2,3-diphenyl-5,7,10-trimethyl-5,10-dihydrophenazine (7 mol percent), and 34 mM 1,1'-bis(phenylpropyl)-4,4'-dipyridinium bis (tetrafluoroborate) in propylene carbonate is deoxygenated with dry nitrogen.

Application of 1.2V across the electrochromic device containing the electrochromic medium of Example 6 results in uniform coloration. The device changes from colorless to blue-gray tint. There is no staging noticed during darkening or clearing.

EXAMPLE 7 AND COMPARATIVE EXAMPLE C7

Electrochromic media containing the electrochromic compound compositions shown below are prepared in propylene carbonate and deoxygenated with dry nitrogen.

| | |
|---|---|
| Comparative Example 7) | 28mM 2-vinyl-5,10-dimethyl-5,10-dihydrophenazine, 34mM 1,1'-bis(phenylpropyl)-4,4'-dipyridinium bis(tetrafluoroborate). |
| Example 7) | 28mM 2-vinyl-5,10-dimethyl-5,1-dihydrophenazine, 4mM 1,1'-bis(3,5-dimethylphenyl)-4,4'-dipyridinium bis(tetrafluoroborate) (14 mol percent), 30mM 1,1'-bis(phenyl-propyl)4,4'-dipyridinium bis(tetrafluoroborate). |

Application of 1.2V across each of the electrochromic devices results in uniform coloration. The device containing the electrochromic medium of Comparative Example 7 changes from light yellow to dark purple, while the device containing the electrochromic medium of Example 7 changes from light yellow to dark gray. There is no staging noticed during darkening or clearing.

EXAMPLE 8 AND COMPARATIVE EXAMPLE C8

Electrochromic media containing the electrochromic compound compositions shown below are prepared in propylene carbonate and deoxygenated with dry nitrogen.

| | |
|---|---|
| Comparative Example C8) | 28mM 2,5,7,10-tetramethyl-5,10-dihydrophenazine, 34mM 1,1'-bis(phenylpropyl)-4,4'-dipyridinium bis(tetrafluoroborate). |
| Example 8) | 28mM 2,5,7,10-tetramethyl-5,10-dihydrophenazine, 4mM 1,1'-diphenyl-4,4'-dipyridinium bis(tetrafluoroborate), 30mM 1,1'-bis(phenylpropyl)-4,4'-dipyridinium bis (tetrafluoroborate)( 12 mol percent). |

Application of 1.2V across each of the electrochromic devices results in uniform coloration. The device containing the electrochromic medium of Comparative Example 8 changes from light yellow to dark green, while the device containing the electrochromic medium of Example 8 changes from light yellow to dark blue-gray. There is no staging noticed during darkening or clearing.

Examples 1 and 2 and the corresponding direct comparative examples C1 and C2 demonstrate that relatively small amounts of a more easily oxidizable anodic electrochromic compound, about 28 mol percent, when employed with an electrochromic compound of higher redox potential, makes a significant contribution to the overall device coloration. Examples 3–6 illustrate the benefits of employed anodic electrochromic compounds in minor amounts which allow preparation of devices having a blue-gray tint upon activation. Examples 7 and 8 and direct comparative examples C7 and C8 demonstrate that minor quantities of more easily reducible electrochromic compounds, about 11 mol percent of total cathodic electrochromic compounds, make a significant contribution to device color when employed with a cathodic electrochromic compound of higher redox potential.

What is claimed is:

1. An electrochromic medium capable of producing a pre-selected color, comprising at least three electroactive compounds, two of which are of the same redox type and another which is of a complementary redox type, where one of said two electroactive compounds of the same redox type has a more easily accessible electrochemically activated redox state than the other by minimally 30 mV, and where two of the at least three electroactive compounds are electrochromic.

2. The electrochromic medium of claim 1, where said at least three electroactive compounds comprise at least two anodic electroactive compounds and at least one cathodic electroactive compound.

3. The electrochromic medium of claim 2, wherein said at least one cathodic electrochromic compound is a dipyridinium compound.

4. The electrochromic medium of claim 2, wherein said at least one anodic electrochromic compound is a 5,10-dihydrophenazine compound.

5. The electrochromic medium of claim 2, wherein said electroactive compounds are contained in a polar organic solvent.

6. The electrochromic medium of claim 1, where said at least three electroactive compounds comprise at least two cathodic electroactive compounds and at least one anodic electroactive compound.

7. The electrochromic medium of claim 6, wherein said at least one cathodic electrochromic compound is a dipyridinium compound.

8. The electrochromic medium of claim 6, wherein the said electroactive compounds are contained in a polar organic solvent.

9. The electrochromic medium of claim 1, where said more easily accessible electrochemically activated state is more accessible by minimally 40 mV.

10. The electrochromic medium of claim 1, wherein said electroactive compound of the same redox type whose redox state is more easily accessible is present in the amount of 28 mol percent or less of the total electrochromic compounds of the same type.

11. The electrochromic medium of claim 1, wherein said electroactive compound of the same redox type whose redox state is more easily accessible is present in the amount of 25 mol percent or less of the total electrochromic compounds of the same type.

12. The electrochromic medium of claim 1, wherein said electroactive compound of the same redox type whose redox state is more easily accessible is present in the amount of 20 mol percent or less of the total electrochromic compounds of the same type.

13. The electrochromic medium of claim 1, where said electrochromic medium does not exhibit staging.

14. The electrochromic medium of claim 1, wherein said electrochromic compounds are selected from 5,10-dihydrophenazine compounds and dipyridinium compounds.

15. The electrochromic medium of claim 1, wherein said electrochromic medium further comprises a cross-linked polymer matrix.

16. An electrochromic display device light filter, comprising:

(a) a cavity containing the electrochromic medium of claim 1, said cavity defined by;

(b) a first transparent substrate which is an integral part of a display device, said substrate having deposited thereon, a transparent conductive electrode on the side of said substrate defining said cavity;

(c) a second substrate having deposited thereon a transparent conductive electrode on the side of said second substrate defining said cavity; and (d) a seal disposed generally along the peripheral edge of said first and second substrate.

17. The electrochromic display device light filter of claim 16, where said display device is a CRT.

18. The electrochromic display device light filter of claim 16, where said light filter produces a gray color.

19. The electrochromic display device light filter of claim 16, wherein said display device filter is positioned between said display device and a human operator.

20. An electrochromic medium capable of producing a pre-selected color, comprising at least three electroactive compounds, two of which are of the same redox type and another which is of a complementary redox type, where one of said two electroactive compounds of the same redox type has a more accessible electrochemically activated redox state and is present at a concentration of less than 28 mol percent of the total electroactive compounds of the same redox type, and where two of the at least three electroactive compounds are electrochromic.

21. The electrochromic medium of claim 20, wherein said at least three electroactive compounds comprise at least two anodic electroactive compounds and at least one cathodic electroactive compound.

22. The electrochromic medium of claim 20, wherein said at least three electroactive compounds comprise at least two cathodic electroactive compounds and at least one anodic electroactive compound.

23. The electrochromic medium of claim 20, wherein the first of said at least two electroactive compounds of the same redox type has a more easily accessible electrochemically activated redox sate than the other by minimally 30 mV.

24. The electrochromic medium of claim 20, wherein the first of said at least two electroactive compounds of the same redox type has a more easily accessible electrochemically activated redox state than the other by minimally 40 mV.

25. The electrochromic medium of claim 20, wherein said electrochromic medium further comprises a cross-linked polymer matrix.

26. The electrochromic medium of claim 20, where said electrochromic medium does not exhibit staging.

27. The electrochromic medium of claim 20, where said pre-selected color is gray.

28. An electrochromic display device light filter, comprising:
  (a) a cavity containing the electrochromic medium of claim 20, said cavity defined by;
  (b) a first transparent substrate which is adapted to be positioned onto a display device, said substrate having deposited thereon a transparent conductive electrode on the side of said substrate defining said cavity;
  (c) a second substrate having deposited thereon a transparent conductive electrode on the side of said second substrate defining said cavity; and
  (d) a seal disposed generally along the peripheral edge of said first and second substrate.

29. The electrochromic display device light filter of claim 28, where said display device is a CRT.

30. The electrochromic display device light filter of claim 28, where said light filter produces a gray color.

31. The electrochromic display device light filter of claim 28, further comprising a display device placed on an opposed side of said display device filter and a human operator.

32. An electrochromic medium capable of producing a pre-selected color, comprising at least three electroactive compounds, two of which are of the same redox type and another which is of a complementary redox type, where one of said two electroactive compounds of the same redox type has a more easily accessible electrochemically activated redox state and contributes to the absorption spectrum of the electrochemically activated state of the medium to a greater extent expected based solely on its abundance in the medium.

* * * * *